Figure 1:
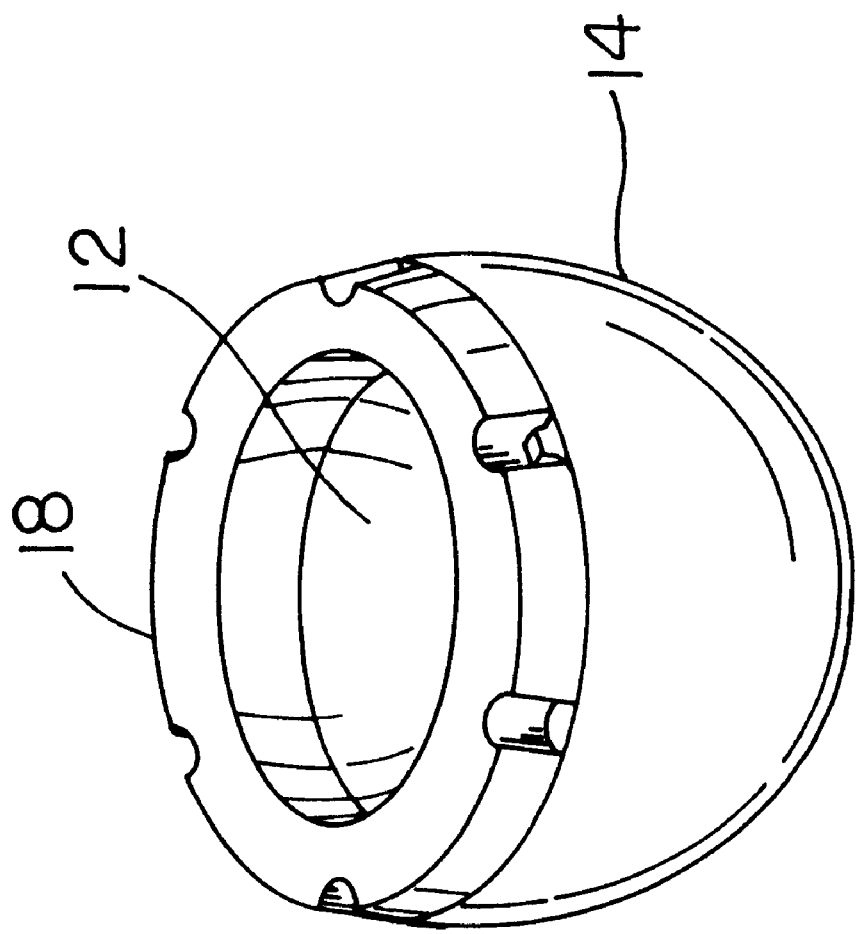

United States Patent [19]
Cook et al.

[11] Patent Number: 5,989,293
[45] Date of Patent: Nov. 23, 1999

[54] ACETABULAR CUP KIT FOR USE DURING HIP REPLACEMENT SURGERY

[75] Inventors: Kevin S. Cook, Warsaw; Stephen Rozow, III, Milford, both of Ind.

[73] Assignee: Bristol-Myers Squibb Co., New York, N.Y.

[21] Appl. No.: 09/118,579

[22] Filed: Jul. 17, 1998

[51] Int. Cl.⁶ .................................................. A61F 2/34
[52] U.S. Cl. ............................................................ 623/22
[58] Field of Search ................................ 623/16, 18, 22, 623/23, 19

[56] References Cited

U.S. PATENT DOCUMENTS

| | | |
|---|---|---|
| B1 438,090 | 9/1993 | Ramos ........................................ 623/22 |
| 3,584,318 | 6/1971 | Scales et al. . |
| 3,698,017 | 10/1972 | Scales et al. . |
| 3,818,512 | 6/1974 | Shersher . |
| 3,848,272 | 11/1974 | Noiles . |
| 3,863,273 | 2/1975 | Averill . |
| 3,875,593 | 4/1975 | Shersher . |
| 3,916,451 | 11/1975 | Buechel et al. . |
| 3,978,528 | 9/1976 | Crep . |
| 4,004,300 | 1/1977 | English . |
| 4,044,403 | 8/1977 | D'Errico . |
| 4,135,517 | 1/1979 | Reale . |
| 4,159,544 | 7/1979 | Termanini . |
| 4,172,296 | 10/1979 | D'Errico . |
| 4,241,463 | 12/1980 | Khovaylo . |
| 4,365,358 | 12/1982 | Judet et al. . |
| 4,770,658 | 9/1988 | Geremakis ................................ 623/22 |
| 4,784,663 | 11/1988 | Kenna ........................................ 623/22 |
| 4,919,674 | 4/1990 | Schelhas ................................... 623/22 |
| 5,019,105 | 5/1991 | Wiley ........................................ 623/22 |
| 5,263,988 | 11/1993 | Huebner .................................... 623/22 |
| 5,314,491 | 5/1994 | Thongpreda et al. .................... 623/22 |
| 5,425,778 | 6/1995 | Zichner et al. ........................... 623/22 |
| 5,507,826 | 4/1996 | Besselink et al. ........................ 623/22 |

OTHER PUBLICATIONS

Zimmer Engineering Drwgs Showing a Custom All–Poly Liner for a Metal Shell First Sold in Oct. 1994.

The Zimmer MultiPolar—The Singular Choice in Biopolar Cups 97–5003–01 1990 (Zimmer, Inc.).

Mallory–Head Hip Program—Constrained Acetabular System Y–BMT–456/021596/M (Biomet).

Salvage of a Recurrently Dislocating Total Hip Prosthesis with Use of a Constrained Acetabular Component (The Journal of Bone and Joint Surgery, Inc., 1998).

Failure of a Constrained Acetabular Prosthesis of a Total Hip Arthroplasty (The Journal of Bone and Joint Surgery, Inc., 1998).

*Primary Examiner*—David J. Isabella
*Attorney, Agent, or Firm*—Cary R. Reeves

[57] ABSTRACT

An acetabular cup kit for use during hip replacement surgery includes a polar component with a socket for receiving a femoral head of a femoral prosthesis. A metal shell has a cavity which is configured for receiving the polar component therein. The metal shell also includes an annular face bounding the cavity. A metal ring is attachable with the metal shell at the annular face. The metal ring is configured to retain the polar component within the cavity when attached with the metal shell. The metal ring includes at least one secondary fixation device, such as a flange, allowing fixation of the metal ring with a pelvic bone. A plastic ring is also attachable with the metal shell at the annular face. The plastic ring is configured to retain the polar component within the cavity when attached with the metal shell.

9 Claims, 5 Drawing Sheets

ACETABULAR CUP KIT FOR USE DURING HIP REPLACEMENT SURGERY

BACKGROUND OF THE INVENTION

1. Field of the Invention

The present invention relates to an orthopaedic implant assembly, and, more particularly, to an acetabular cup assembly used during hip replacement surgery.

2. Description of the Related Art

An orthopaedic implant assembly in the form of an acetabular cup assembly is implanted within a prepared acetabulum of a patient and receives the femoral head of a femoral implant. The acetabular cup includes an outside diameter which is placed against the prepared pelvis and an inside diameter which receives the femoral head. A polymeric bearing surface may be disposed at the inside diameter of the cup because of improved wear and reduced friction properties associated therewith.

An acetabular cup may include a portion defining an annular face or rim radially adjacent to the femoral head receiving cavity which is either formed from metal or plastic. Forming the rim from a plastic material has an advantage of preventing metal-to-metal contact between the neck of the femoral implant and the rim when the femoral implant is articulated within the acetabular cup. On the other hand, a metal rim is more rigid and allows secondary fixation devices such as bone screws to be placed through flanges or straps which project radially from the cup. Regardless of whether the rim surrounding the femoral head receiving cavity is formed from metal or plastic, the acetabular cup is formed as a unitary structure which is then implanted into a prepared acetabulum in the patient. The surgeon is not given a choice of whether to use the cup portion with a metal rim or a plastic rim surrounding the femoral head receiving cavity.

What is needed in the art is an acetabular cup with modular components allowing the surgeon to choose either a metal rim or a plastic rim surrounding the femoral head receiving cavity immediately prior to implantation into a prepared acetabulum, thereby allowing the surgeon to optimize the configuration of the implanted acetabular cup during surgery.

SUMMARY OF THE INVENTION

The present invention provides an acetabular cup kit with a polar component which is selectively attachable to either a metal ring or a plastic ring, dependent upon criteria associated with a particular implant procedure, such as the condition of a pelvic bone, personal preference, etc.

The invention comprises, in one form thereof, an acetabular cup kit for use during hip replacement surgery. The kit includes a polar component with a socket for receiving a femoral head of a femoral prosthesis. A metal shell has a cavity which is configured for receiving the polar component therein. The metal shell also includes an annular face bounding the cavity. A metal ring is attachable with the metal shell at the annular face. The metal ring is configured to retain the polar component within the cavity when attached with the metal shell. The metal ring includes at least one secondary fixation device, such as a flange, allowing fixation of the metal ring with a pelvic bone. A plastic ring is also attachable with the metal shell at the annular face. The plastic ring is configured to retain the polar component within the cavity when attached with the metal shell.

An advantage of the present invention is that the acetabular cup may be selectively assembled with either a metal ring or a plastic ring at the discretion of the surgeon.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 1 is a perspective, assembled view of an embodiment of an acetabular cup kit of the present invention in an assembled state, FIG. 2 is an exploded, perspective view of an acetabular cup kit of the present invention showing both the plastic ring and metal ring which may be selectively assembled with the polar component and metal shell by the surgeon;

FIG. 3 is a top view of the acetabular cup kit of FIG. 2 with the metal ring being selectively assembled;

FIG. 4 is a top view of the acetabular cup kit of FIG. 2 with the plastic ring being selectively assembled;

FIG. 5 is a sectional view taken along line 5—5 in FIG. 4;

FIG. 6 is a sectional view generally taken along line 6—6 in FIG. 3; and FIG. 7 is a side, sectional view of another embodiment of an acetabular cup kit of the present invention in an assembled state.

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Referring now to the drawings, there is shown an embodiment of an acetabular cup kit 10 of the present invention for use during hip replacement surgery, such as a primary or revision surgery. Acetabular cup kit 10 generally includes a polar component 12, a metal shell 14, a metal ring 16 and a plastic ring 18. Acetabular cup kit 10 allows a surgeon to selectively utilize polar component 12 and metal shell 14 with either of metal ring 16 or plastic ring 18 depending upon various factors, such as the condition of the pelvic bone, preference of the surgeon, etc.

Polar component 12 includes a socket 20 which is sized and shaped for receiving a femoral head of a femoral prosthesis (not shown) therein. Polar component 12 is formed from a plastic material which has good wear properties and a relatively low coefficient of friction. In the embodiment shown, polar component 12 is formed from ultra-high-molecular-weight-polyethylene (UHMWPE). Polar component 12 has an annular surface 22 which surrounds socket 20, and defines an annular lip 24 with an inside diameter positioned generally at the equator of socket 20. An abutment shoulder 26 at the exterior periphery of polar component 12 engages with a portion of metal ring 16 or plastic ring 18 to hold polar component 12 in place when assembled, as will be described in more detail hereinafter.

Metal shell 14 has a cavity 28 which is configured for receiving polar component 12 therein. That is, the inside diameter of cavity 28 is slightly larger than or substantially the same size as the outside diameter of polar component 12, whereby polar component 12 may be received within cavity 28 with a predetermined clearance or no clearance therebetween. An annular face 30 surrounds cavity 28 and is concentric about a longitudinal axis 32. A lock ring 34 positioned close to annular face 30, and substantially concentrically about longitudinal axis 32, allows metal shell 14 to be attached via a snap-lock engagement with either of metal ring 16 or plastic ring 18. Lock ring 34 may either be integrally formed with metal shell 14, or may be a separate ring which is disposed within a slot formed at the inside diameter of metal shell 14 within cavity 28.

Metal shell 14 is configured to provide primary fixation with the prepared acetabulum. For example, metal shell 14 may have a machined inside diameter defining cavity 28, with a porous metal surface on the outside diameter thereof, such as fiber metal, etc. The porous metal, in known manner, allows primary fixation via bony ingrowth or bone cement. Moreover, metal shell 14 may be provided with one or more holes therein which are sized to receive a corresponding fastener such as a bone screw providing primary fixation with the acetabulum. Metal shell 14 includes a pair of male keys 29 which mate with corresponding keyways on metal ring 16 or plastic ring 18, as will be described in more detail.

Figure 2:
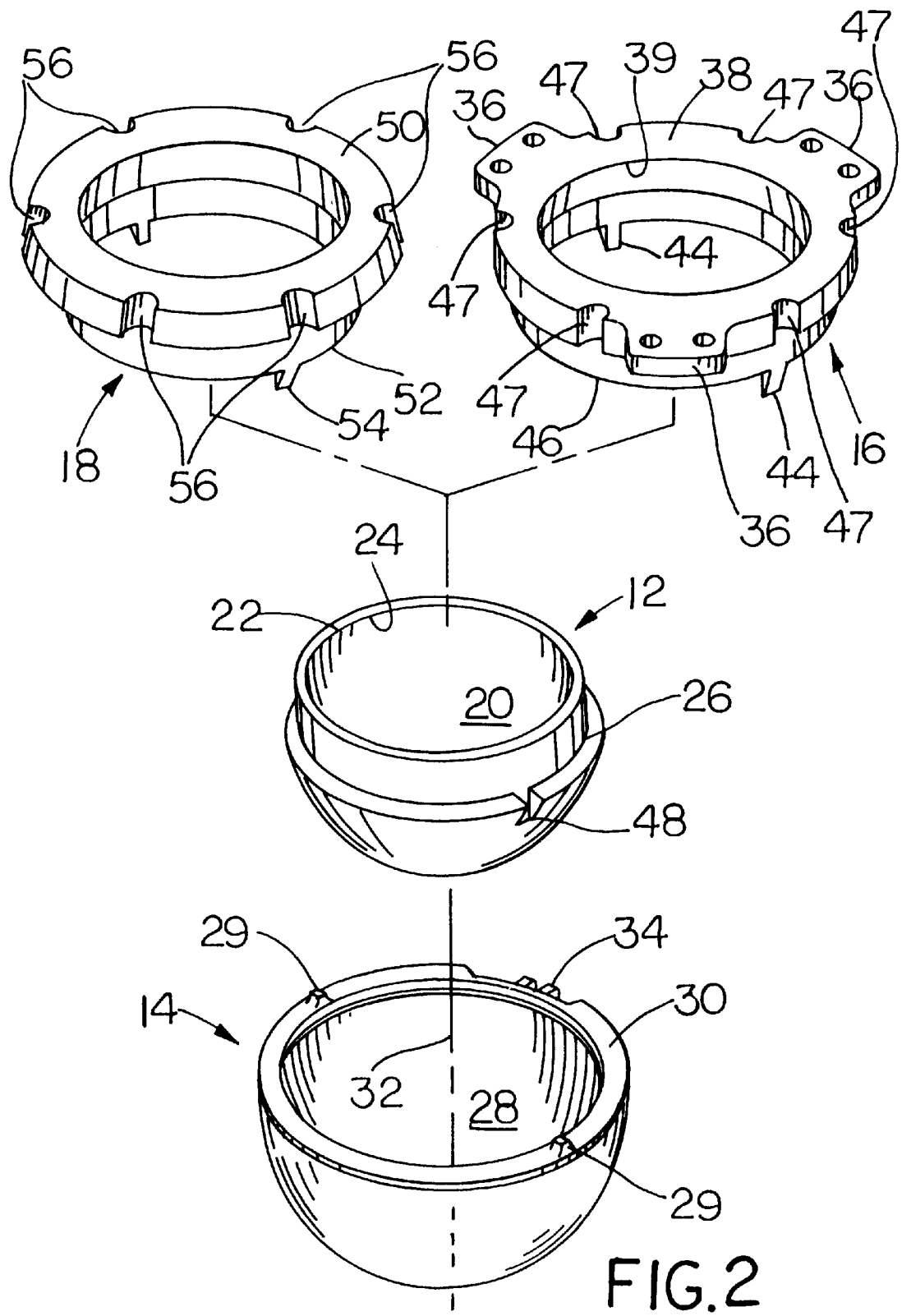
Figure 4:
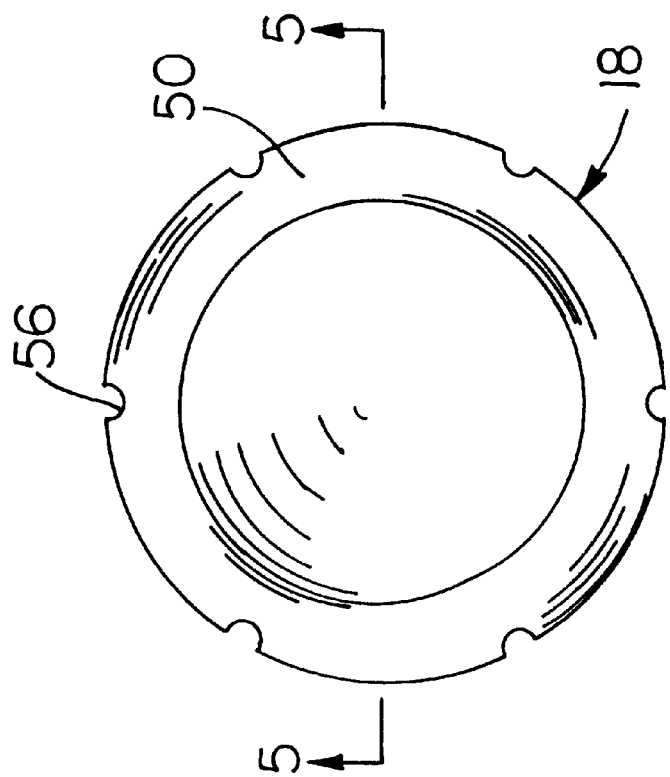
Figure 3:
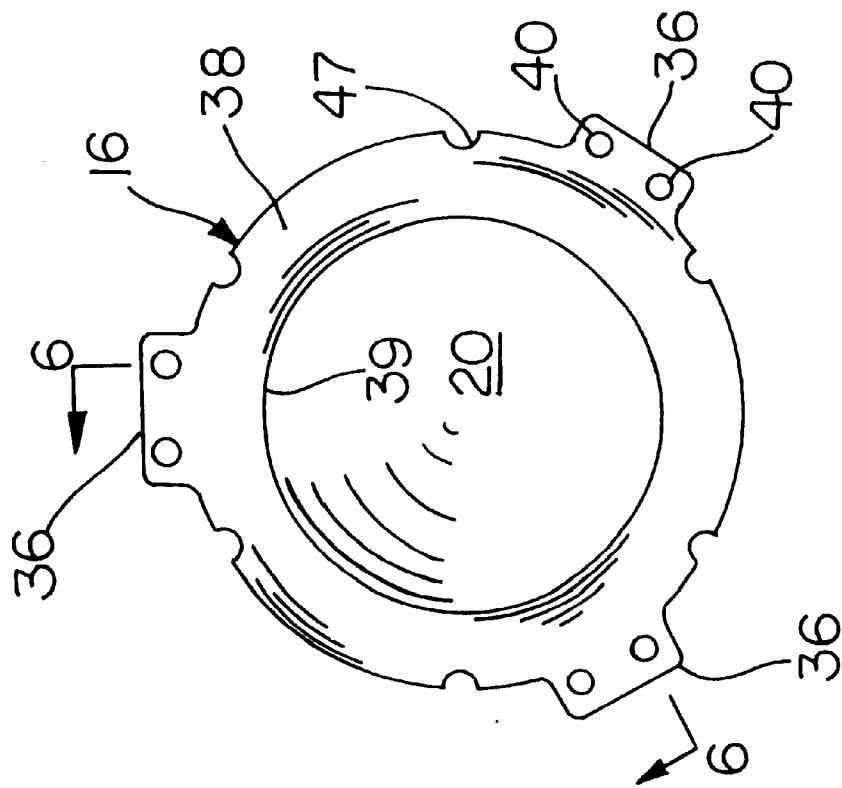
Figure 5:
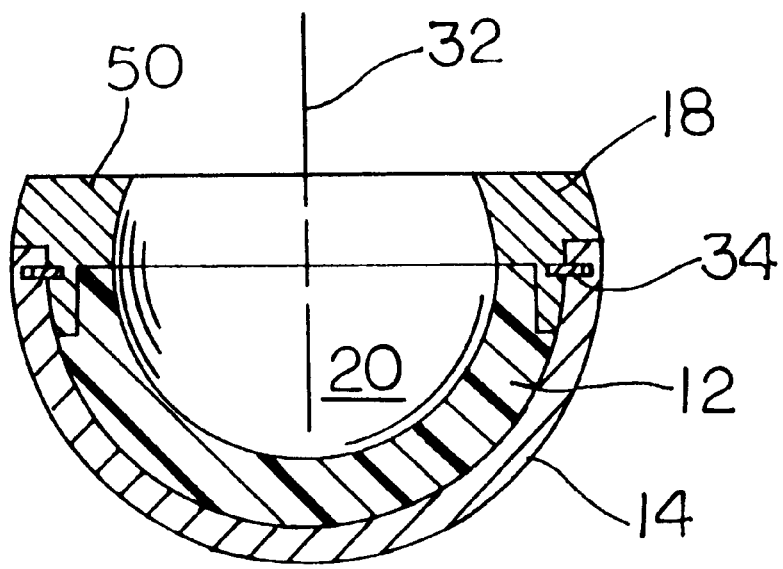
Figure 6:
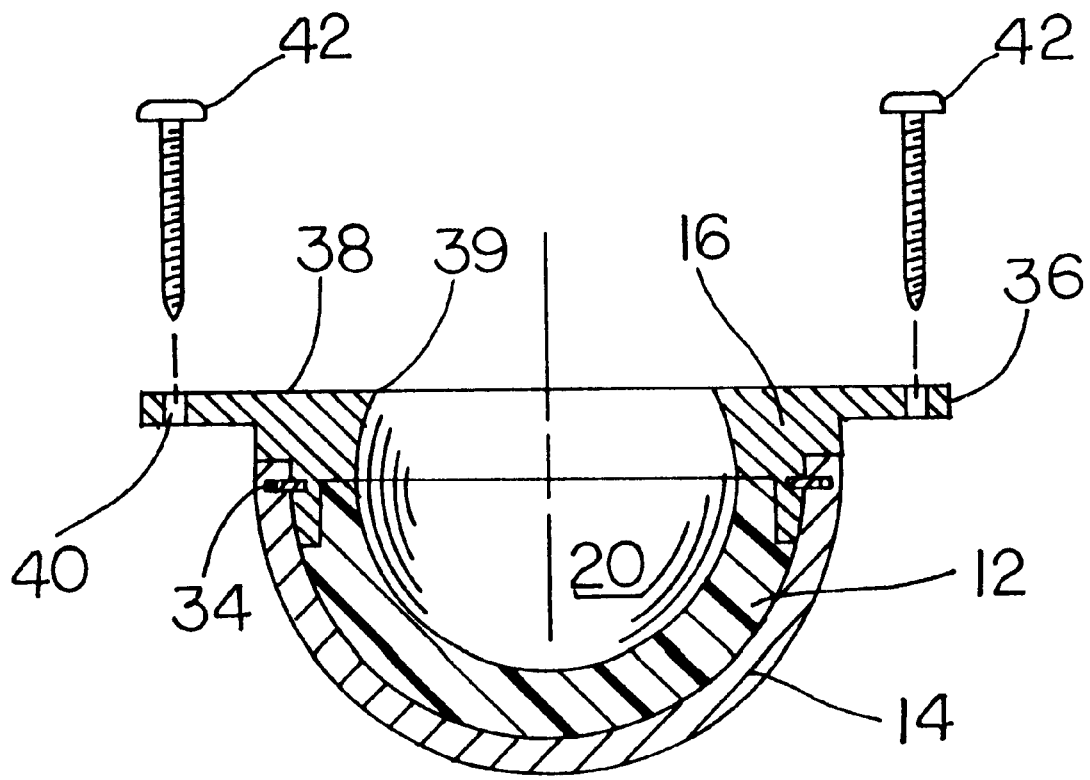

Metal ring 16 is attachable with metal shell 14 at annular face 30, as shown in FIG. 6. Depending upon the condition of the prepared acetabulum, it may be necessary to attach the acetabular cup to the acetabulum with additional fixation devices, such as screws, pins, etc. Because metal ring 16 is formed from a metal which can withstand loading using such fasteners, it is possible to provide secondary fixation of the acetabular cup to the acetabulum, in addition to the primary fixation between metal shell 14 and the acetabulum. Metal ring 16 includes an annular surface 38 at an axial end thereof which surrounds socket 20, and defines an annular lip 39 with an inside diameter which is smaller than the maximum inside diameter of socket 20 at annular lip 24 (FIGS. 5 and 6). The smaller inside diameter of annular lip 39 holds the femoral head of a femoral prosthesis (not shown) within socket 20 and thereby inhibits dislocation of the hip joint by constraining the femoral head. A plurality of flanges 36, such as the three flanges shown in FIGS. 2 and 3, extend radially outwardly from longitudinal axis 32. Each flange 36 includes two holes 40 which are sized to receive fasteners such as bone screws 42 (FIG. 6). Flanges 36 may be of any desired length necessary to allow securement of metal ring 16 with the pelvic bone of the patient.

Metal ring 16 also includes a keying arrangement which mates with a corresponding keying arrangement on polar component 12 to inhibit torsional or rotational movement therebetween when assembled. More particularly, metal ring 16 includes a keying arrangement in the form of two tabs 44 which extend from an abutment face 46 on opposite sides of metal ring 16. Abutment face 46 of metal ring 16 abuts against metal shoulder 26 of polar component 12, and tabs 44 are received within corresponding notches 48 formed in polar component 12. When tabs 44 are received within notches 48, metal ring 16 is prevented from moving in a rotational direction around longitudinal axis 32, relative to polar component 12.

Metal ring 16 also includes female keyways 47 which mate with male keys 29 of metal shell 14 and prevent relative movement therebetween. Male keys 29 are sized to slightly interfere and thereby form an interference fit with female keyways 47 when metal ring 16 is assembled with metal shell 14.

Plastic ring 18 may selectively engage polar component 12 and metal shell 14 in a manner which is similar to that of metal ring 16. To that end, plastic ring 18 includes an annular surface 50, abutment face 52, tabs 54 and female keyways 56 which are similar to annular surface 38, abutment face 46, tabs 44 and female keyways 47 of metal ring 16. However, plastic ring 18 is formed from a suitable plastic material, rather than a metal. Thus, the possibility of the femoral prosthesis contacting another metallic structure which could cause wear or levering of the femoral prosthesis out of the socket are eliminated.

Figure 7:
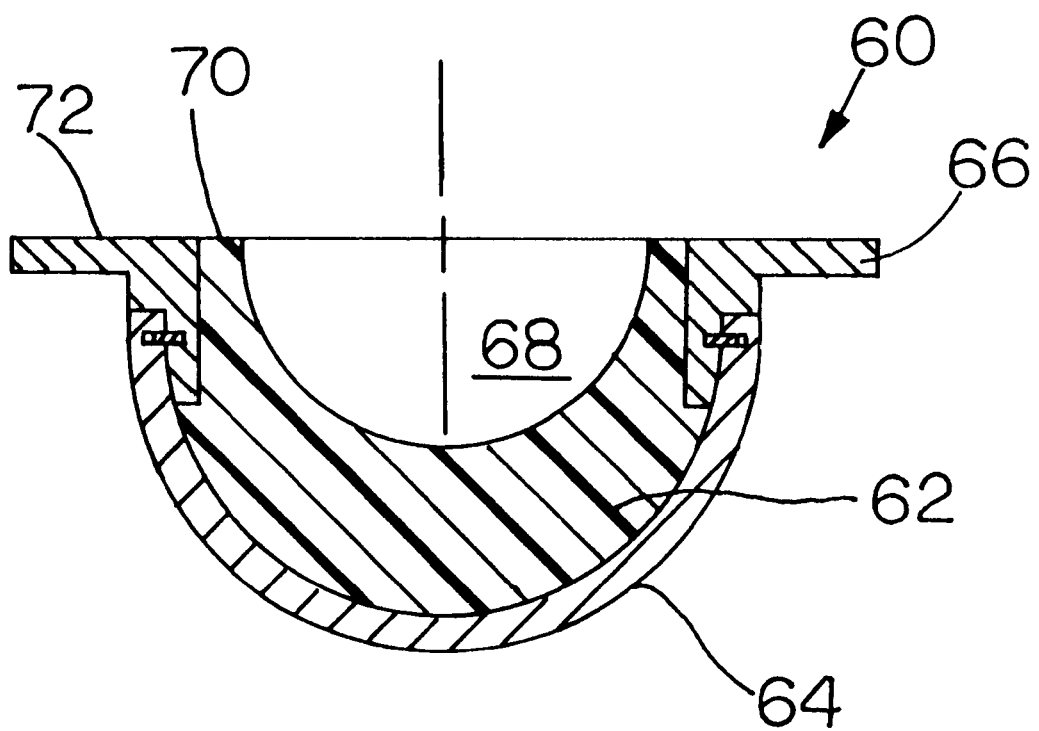

FIG. 7 illustrates another embodiment of an acetabular cup kit 60 of the present invention for use during hip replacement surgery, such as a primary or revision surgery. Acetabular cup kit 60 is similar to acetabular cup kit 10 shown in FIGS. 1–6 and generally includes a polar component 62, metal shell 64 and metal ring 66. Acetabular cup kit 60, similar to acetabular cup kit 10, may also include a plastic ring without flanges (not shown) which mates with polar component 62 and metal shell 64. Acetabular cup kit 60 primarily differs from acetabular cup kit 10 in that it is configured as a non-constrained acetabular cup with the largest diameter opening of socket 68 for the femoral head being at the axial end thereof Additionally, annular surface 70 of polar component 62 is radially within and substantially coplanar with annular surface 72 of metal ring 66.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An acetabular cup kit for use during hip replacement surgery, comprising:

a polar component including a socket for receiving a femoral head of a femoral prosthesis;

a metal shell having a cavity configured for receiving said polar component therein, and an annular face bounding said cavity;

a metal ring attachable with said metal shell at said annular face, said metal ring being configured to retain said polar component within said cavity when attached with said metal shell, said metal ring including at least one secondary fixation device allowing fixation of said metal ring with a pelvic bone; and a plastic ring attachable with said metal shell at said annular face, said plastic ring being configured to retain said polar component within said cavity when attached with said metal shell.

2. The acetabular cup kit of claim 1, wherein said polar component includes a first keying arrangement and each of said metal ring and said plastic ring include a second keying arrangement, said first keying arrangement mating with said second keying arrangement to inhibit movement between said polar component and either of said metal ring and said plastic ring.

3. The acetabular cup kit of claim 2, wherein said first keying arrangement comprises a plurality of notches and wherein said second keying arrangement comprises a plurality of tabs.

4. The acetabular cup kit of claim 1, wherein said metal shell has a longitudinal axis and said secondary fixation device comprises at least one flange extending radially outwardly from said longitudinal axis, each said flange having at least one hole therein for receiving a fastener.

5. The acetabular cup kit of claim 4, wherein said at least one flange comprises a plurality of flanges.

6. The acetabular cup kit of claim 1, wherein said metal shell has a longitudinal axis and wherein said polar component is disposed radially within one of said metal ring and said plastic ring when said one metal ring and plastic ring is attached with said metal shell.

7. The acetabular cup kit of claim 1, wherein each of said metal ring and said plastic ring are configured for abutting said annular face of said metal shell.

8. The acetabular cup kit of claim 7, wherein said metal shell has a longitudinal axis, each of said metal ring and said plastic ring including an abutment face disposed radially within said metal shell, said polar component having an abutment shoulder which abuts said abutment face.

9. The acetabular cup kit of claim 1, wherein said acetabular cup kit comprises a non-constrained cup kit.

* * * * *